United States Patent [19]

Ward

[11] Patent Number: 4,644,803
[45] Date of Patent: Feb. 24, 1987

[54] FORCE MEASUREMENT APPARATUS AND METHOD

[75] Inventor: Roger W. Ward, Salt Lake City, Utah

[73] Assignee: Quartztronics, Inc., Salt Lake City, Utah

[21] Appl. No.: 797,599

[22] Filed: Nov. 13, 1985

Related U.S. Application Data

[62] Division of Ser. No. 506,314, Jun. 21, 1983, Pat. No. 4,574,639.

[51] Int. Cl.⁴ .......................... G01L 1/02; G01L 7/00; G01P 15/08; G01F 1/34
[52] U.S. Cl. .......................... 73/862.58; 73/517 AV; 73/717; 73/861.71; 73/861.47; 177/208; 177/210 FP
[58] Field of Search ............ 73/702, 704, 723, 862.58, 73/862.59, 30, 32 A, 717, 861.47, 861.71, 517 AV; 177/208, 210 FP

[56] References Cited

U.S. PATENT DOCUMENTS

| | | | |
|---|---|---|---|
| 3,216,260 | 11/1965 | Erdely | 73/704 |
| 3,902,365 | 9/1975 | Knauth | 73/32 A |
| 4,126,049 | 11/1978 | Cotter | 73/702 |
| 4,219,090 | 8/1980 | Dayton | 177/208 |

FOREIGN PATENT DOCUMENTS 119221 7/1984 Japan ..................... 177/210 FP

Primary Examiner—Stewart J. Levy
Assistant Examiner—John E. Chapman, Jr.
Attorney, Agent, or Firm—Thorpe, North & Western

[57] ABSTRACT

Fluid density measuring apparatus and method for directly measuring fluid density or indirectly measuring force, acceleration, flow velocity, differential pressure and other parameters affecting the apparatus. The apparatus includes a bellows and a generally rigid hollow housing having openings through which fluid may flow to the interior of the housing, and a vibratory single-ended tuning fork mounted in the housing. The apparatus also includes circuitry for causing the tines of the tuning fork to resonate, for example, 180 degrees out of phase in a transverse direction, with the frequency of the tines varying with variation in the density of the fluid surrounding the tines. Circuitry is also included for determining the frequency at which the tuning fork tines resonate. When the density of the fluid into which the housing is placed changes, the frequency of vibration of the tines of the tuning fork is caused to change to provide a measure of the density change.

12 Claims, 8 Drawing Figures

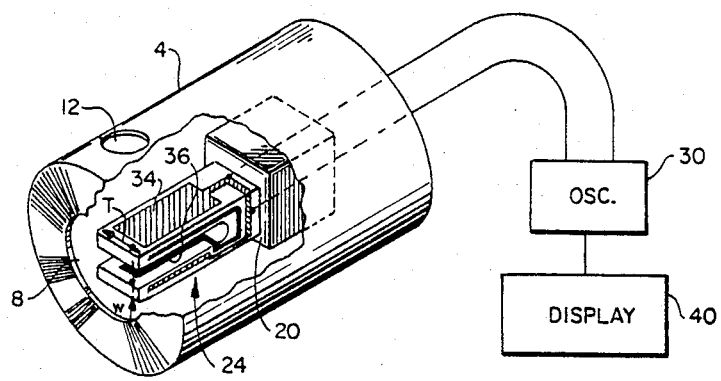
Fig. 1
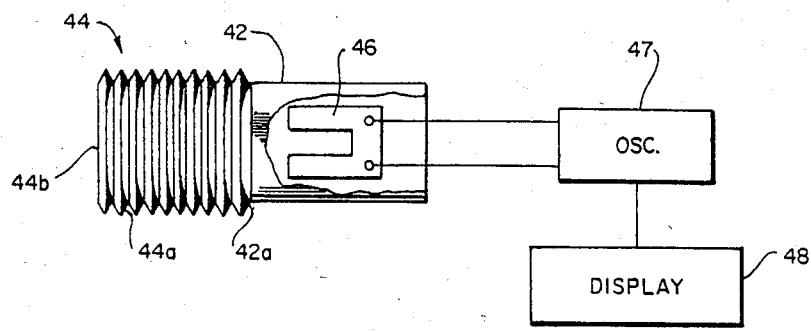
Fig. 2
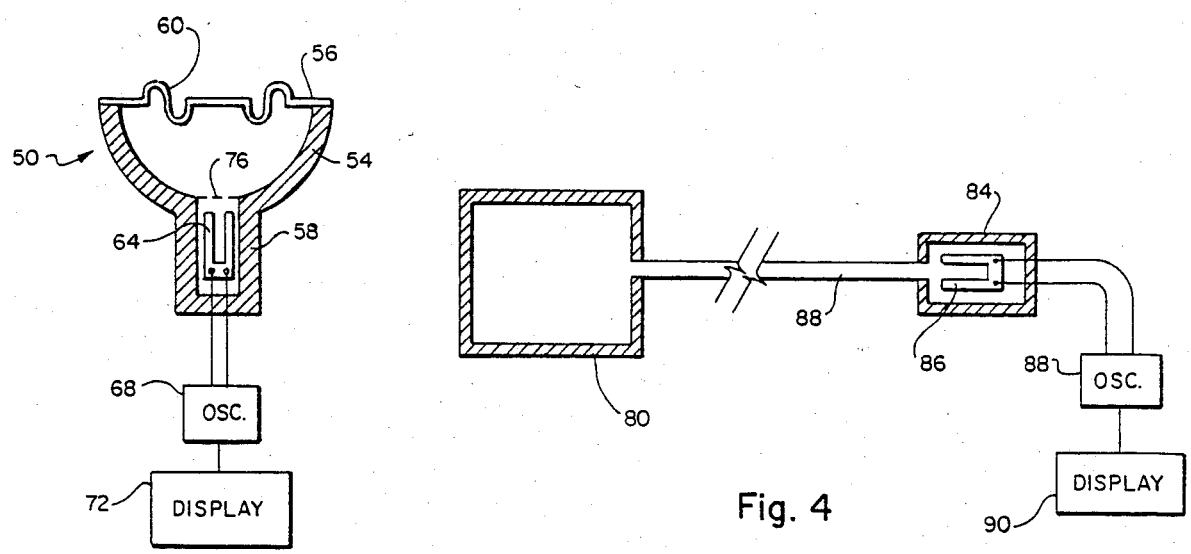
Fig. 3
Fig. 4

FORCE MEASUREMENT APPARATUS AND METHOD

This application is a division of application Ser. No. 06/506,314, filed 6/21/83, now U.S. Pat. No. 4,574,639.

BACKGROUND OF THE INVENTION

This invention relates to a method and apparatus for measuring fluid density and for measuring parameters which may cause the density of the fluid to change.

It has been known for some time that a vibratory element, such as a quartz crystal, when exposed to a gas will change its frequency as the gas pressure changes. See, for example, M. A. Cotter, U.S. Pat. No. 4,126,049, J. W. Stansfeld, U.S. Pat. No. 4,232,544, P. N. Potter, U.S. Pat. No. 4,178,804, "Vacuum Microbalance Techniques", Edited by Klaus H. Behrndt, 1966, Plenum Press, N.Y., and A. Genis and D. E. Newell, "Using The X-Y Flexure Watch Crystal as a Pressure-Force Transducer" delivered at the Thirty First Annual Frequency Control Symposium, Atlantic City, N.J., June, 1977. Although these references recognize that the frequency of a vibratory element will change with a change in pressure of the gas surrounding the element, none recognized or disclosed that gas density measurement could be utilized as the mechanism for measuring pressure, and thus none recognized the full potential of gas density determination as a vehicle for measuring a variety of other parameters such as temperature, acceleration, flow, force, differential pressure, etc. One prior art reference, *Theory of Vibrating Systems and Sound*, by Irving B. Crandell, Von Nostrand, 1926, pp. 124-133, disclosed that the frequency of a vibrating string or rod would change with a change in density of the medium in which the string was placed, but failed to recognize how this phenomenon could be employed in practice and, in fact, misleadingly stated that the change in frequency resulting from a change in density would not be great unless the density of the medium were comparable to that of the rod.

It has been discovered that a principal mechanism by which a flexure or torsional mode vibratory element exposed to a fluid (liquid or gas) is caused to change its frequency is not an intrinsic change in pressure but rather is a change in the density of the fluid. The effect is equivalent to that of adding mass to the vibratory element (increase in density) or taking mass from the vibratory element (decrease in density) to respectively reduce or increase the frequency of vibration. Viewed another way, the effect may be likened to that of an object "flapping in the wind". It has been found that when the surface area of the object normal to the direction of movement or vibration of the object is increased, the "pushing" of the fluid by the object becomes more difficult resulting in a slowing of the vibration, and vice versa. Recognizing this mechanism allows for optimizing the sensitivity of vibratory devices used for measuring density directly or for measuring other parameters such as pressure, temperature, etc. In particular, the greater the surface area of the vibratory element, the greater will be the sensitivity of the frequency of vibration to fluid density changes. Also, by proper selection of the working fluid in which the vibratory element is placed, different measurement objectives can be achieved. For example, in a gas density device, use of a more dense gas such as argon will give rise to greater sensitivity, whereas use of a less dense gas, such as helium, will allow detection of density (and thus pressure or other parameter) changes over a wider range.

The above will become more apparent from a mathematical analysis of the effect fluid density has on a vibratory element. The pressure due to the frontal area of a rectangular bar having a thickness T and a width w, which is vibrating in the w direction, moving ambient fluid is given by:

$$P = -2\pi f r U_0 TC \sin(2\pi ft), \quad (1)$$

where f is the frequency of vibration, r is the density of the ambient fluid, $U_0$ is the peak vibration velocity of the bar in the w direction, and C is a shape factor for edge effects and has a value near unity. The force F per unit length acting on the bar due to the pressure is 2PT, since both sides of the bar are acting on the fluid. Therefore, $$F = -4\pi f r U_0 T^2 C \sin(2\pi ft). \quad (2)$$

Since the velocity U of the vibrating bar is related to the displacement $Y = Y_0 \sin(2\pi ft)$ by:

$$U = 2\pi f Y_0 \cos(2\pi ft), \quad (3)$$

then the force F per unit length is given by:

$$F = -8\pi^2 f^2 r Y_0 T^2 C \sin(2\pi ft). \quad (4)$$

The conventional equation for equilibrium of a laterally vibratintg beam with the force F, from equation 4, added to the inertial forces is:

$$EI \frac{d^4 Y}{dx^4} + (r_q Tw + 2rT^2 C) 4\pi^2 f^2 Y = 0, \quad (5)$$

where E, I, and $r_q$ are Young's Modulus, moment of inertia, and density of the vibrating beam respectively. The resonant frequency $f_0$, for r=0 (no ambient fluid), is thus perturbed by the added term $2rT^2C$ in equation 5. The added term is of the form of an added mass per unit length, just as $r_q Tw$ is the mass per unit length of the bar. The resulting resonant frequency f, from equation 5, is given by $$(f/f_0)^2 = \frac{1}{1 + \frac{2rTC}{r_q w}}. \quad (6)$$

For small perturbations, $$\frac{f}{f_0} = 1 - \frac{rTC}{r_q w}, \quad (7)$$

or $$(f - f_0)/f_0 = rTC/r_q w.$$

From the last equation, it is apparent that the frequency of a vibrating element is substantially linearly dependent upon the density of the working fluid and that increased sensitivity of a vibratory element can be achieved by both increasing the thickness-to-width ratio of the vibrating bar and selecting a more dense fluid as the working medium.

SUMMARY OF THE INVENTION

It is an object of the invention to provide a highly sensitive apparatus and method for measuring directly density and changes in density of fluid to which the apparatus is exposed or other parameters such as pressure, temperature, etc.

It is another object of the invention to provide such apparatus and method in which measurement over large scale ranges can be achieved or high resolution can be obtained.

It is a further object of the invention to provide such apparatus and method which is simple in construction, rugged, and inexpensive.

It is an additional object of the invention to provide such apparatus and method in which sensitivity can be controlled by appropriate selection of the dimensions of the vibratory element.

The above and other objects of the invention are realized in a specific illustrative embodiment of a fluid density measurement device which includes a generally rigid hollow housing, and an elongate bar mounted in the housing and adapted to vibrate in the flexure mode, where the bar has a thickness T to width w ratio of $T/w \geq 0.1$, or in the torsional mode, where the bar has a generally rectangular cross-section. The housing includes openings through which fluid may enter to contact the bar. Circuitry is provided for causing the bar to resonate, with the frequency of resonation varying with variation in the density of the fluid surrounding the bar. To measure the density of a fluid, the device is simply placed in the fluid so that the fluid enters the housing and surrounds the bar. The resulting change in the resonant frequency of vibration of the bar is proportional to the change in density of the fluid.

The device can be adapted to measure a variety of other parameters such as pressure, differential pressure, temperature, acceleration, force, flow velocity, etc. For example, by sealing a movable wall over the openings of the housing so that as the wall moves, the volume in the housing varies, and placing a gas in the housing, pressures exterior to the housing can be measured. That is, as the exterior pressure varies, the wall is caused to move to vary the volume in the housing and thus the density of the gas and this, in turn, causes the frequency of vibration of the bar to vary. Appropriate selection of the gas contained in the housing can provide either a substantially full scale range measurement for the pressures but with less resolution, or a smaller scale range measurement with greater resolution. For example, use of a more dense gas will yield greater resolution, whereas use of a less dense gas will provide a more full scale range measurement.

In accordance with one aspect of the invention, a single ended tuning fork configuration is employed as the vibratable element. The desired thickness-to-width ratio of the tines of the tuning fork may be readily provided with the single ended tuning fork configuration.

BRIEF DESCRIPTION OF THE DRAWINGS

The above and other objects, features and advantages of the invention will become apparent from a consideration of the following detailed description presented in connection with the accompanying drawings in which:

FIG. 1 is a perspective, partially cut away view of a fluid density measuring device made in accordance with the principles of the present invention;

FIG. 2 is a side, elevational, partially cut-away view of a gas density/pressure transducer utilizing a bellows as the pressure transmitting element;

FIG. 3 shows a side, cross-sectional view of a gas density/pressure transducer utilizing a diaphragm as the pressure transmitting element;

FIG. 4 is a side, cross-sectional view of a gas density/temperature transducer made in accordance with the principles of the present invention;

DETAILED DESCRIPTION

Figure 5:
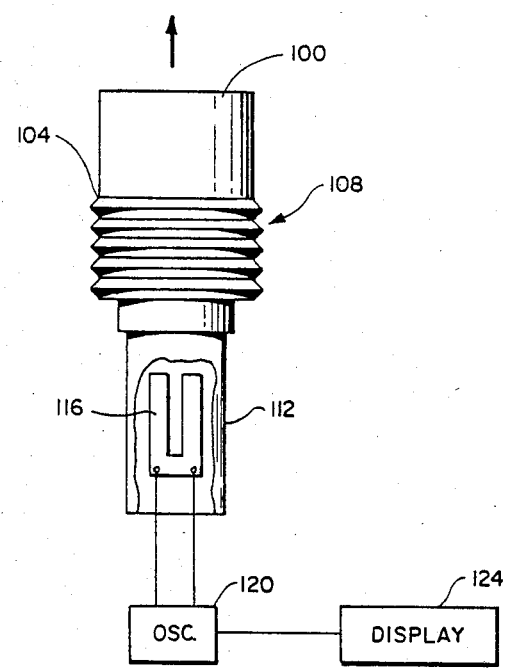
FIG. 5 is a side, elevational, partially cut-away view of a gas density/acceleration transducer.

FIG. 1 shows one embodiment of a fluid density measurement device which takes advantage of the fluid density/frequency of vibration phenomenon. The device includes a generally hollow cylindrical (but other shapes could also be utilized) housing 4. The housing has an opening 8 at one end and another opening 12 on the side to allow fluid to which the housing is exposed to flow into the housing. The housing 4 may be made of any material sufficiently rigid to provide protection for the apparatus which will be mounted in the housing. Openings in the housing may be provided at any locations sufficient to allow fluid to enter the housing.

Disposed in the housing 4 and mounted thereto by way of a mounting base 20 is a single ended vibratable tuning fork 24 having a pair of tines joined together at one end and maintained in a generally spaced-apart, parallel arrangement. The thickness of the tines is given by T and the width is given by w as indicated in FIG. 1. The tuning fork 24 may be made integral with the mounting block 20, or it may be made separate and then mounted on the mounting block 20 which, in turn, is mounted to the inside, bottom wall of the housing 4. This could be done by a suitable adhesive or other fastening devices. Advantageously, the tuning fork 24 is made of quartz, and the mounting base 20 is a nonconducting material such as glass.

An oscillator circuit 30 is coupled to thin electrode films or coatings 34 and 36 disposed on various surfaces of the tuning fork 24 in a conventional way, as shown in the drawing. Application of A.C. signals by the oscillator 30 to the electrode films 34 and 36 produces stress forces in the tines to cause the tines to vibrate in a transverse direction (flexure mode) in 180° phase opposition. That is, the tines are caused to move in the w direction outwardly away from each other and then inwardly toward each other, etc., in a well known manner and at a characteristic or desired natural resonant frequency. When the density of fluid to which the housing 4 is exposed changes, the frequency of vibration of the tines is caused to change, and the magnitude of the change serves as a measure of the change in density. The oscillator 30 follows in frequency the frequency of the tuning fork 24 and so the change in frequency of the turning fork can be measured by simply measuring the output frequency of the oscillator. A conventional counter and display 40 may be connected to the oscillator 30 to provide a readout of the densities being measured.

Resolution can be improved by increasing the thickness-to-width ratio T/W of the tuning fork tines. However, fabrication problems limit, to a certain extent, the thickness-to-width ratio which may be obtained for quartz crystal tuning forks made by photolithographic processes. It has been found that a thickness-to-width ratio T/w of 0.1 or greater is suitable. Crystals thicker than about 0.25 mm cannot be etched through readily; tines narrower than about 0.12 mm are too narrow to allow proper electrode definition. This limits T/w to about two for photolithographically produced quartz crystal tuning forks. For wire-sawed forks, a thickness of 1 mm and width of 0.12 are practical limits for a T/w ratio of eight.

Although the electrode coatings 34 and 36 of FIG. 1 are arranged to cause the tuning fork 24 to vibrate in the flexure mode, they could be arranged to cause the tuning fork to vibrate in what is called the torsional mode. See R. Dinger, 37th Frequency Control Symposium, Philadelphia, 1982. A change in density of fluid surrounding the tuning fork 24 would also cause a proportional change in frequency of vibration of the tuning fork resonating in the torsional mode, provided the tuning fork tines were not cylindrical in shape. In particular, the tuning fork tines should have rectangular cross-sections for torsional mode operation so that as the tines vibrate, they will push against the fluid in which they are placed.

There are a variety of uses of the device of FIG. 1 including measurement of the extent to which a cavity has been evacuated of gas, measurement of the degree of contamination of a fluid with other fluids or materials (which would cause a change in density), measurement of the density of the air/fuel mixture used in internal combustion engines to assist in maximizing power output and reducing polluting emissions, etc.

FIG. 2 shows an embodiment of a gas density/pressure transducer made in accordance with the present invention. The transducer apparatus includes a generally rigid hollow housing 42, open at one end 42*a*. Sealingly placed over the opening is a bellows 44 having an accordian-like sidewall 44*a* and a generally flat endwall 44*b*. The housing 42 may be made of any rigid material capable of withstanding the fluid pressure to which it would be subjected and, advantageously, capable of withstanding corrosion. For example, stainless steel might be used. The bellows 44 would advantageously be made of a fairly flexible material, at least for the side walls 44*a*, such as electroless nickel. It is desired that the bellows 44 be fairly soft and flexible so that any pressure to which the housing 42 and bellows 44 are subjected will be transmitted to the interior of the housing.

Contained in the housing 42 is a working gas, preferably one of the inert gases such as argon, radon, helium, etc. It is the change in density of this gas which will be measured to provide a measure of the exterior pressure.

A single-ended tuning fork 46 is disposed in the housing 42, and is caused to vibrate in either the flexure or torsional modes by an oscillator circuit 47 which is coupled to a display 48.

If a wide measuring range for the pressures is desired, then a less dense gas such as helium, neon, hydrogen, methane, etc., may be used as the working fluid in the housing 42. Preferably, inert gases would be used to avoid problems of corrosion of the housing 42 or of the vibratory element and its electrodes or other driving mechanism, and of potential combustion problems. If a less dense gas is used, a greater exterior pressure change is needed to produce a given change in the frequency of vibration of the tuning fork 46. Thus, a wide range of pressures may be measured for whatever range of frequency changes is possible with the apparatus. For example, pressures of helium from 0.07 to 700 MPa (Megapascal can be measured with a sensitivity of 36 parts per million per MPa for a tuning fork having T/w $\geq$ 0.75.

If greater sensitivity or resolution is desired, then a more dense gas such as argon, xenon, radon, krypton, etc., may be used as the working fluid in the housing 42. Because such gases are more dense, any change of pressure will cause a more significant change in frequency of vibration of the tuning fork 24 per equation (7), and so even small pressure changes will be detectable. For example, using argon gas, the same tuning fork above has a sensitivity of 360 ppm/MPa over a pressure range of 0.07 to 70 MPa.

As indicated earlier, resolution, whether using a more dense or less dense gas as the working fluid, can be improved by increasing the thickness-to-width ratio T/w of the tuning fork tines. It has been found that a thickness-to-width ratio T/w of 0.5 or greater is suitable regardless of the type of working gas employed. For a higher density gas which results in greater sensitivity, the thickness-to-width ratio may be as low as about 0.1 and still provide suitable results.

FIG. 3 shows an alternative embodiment of a fluid density/pressure transducer. This embodiment includes a housing 50, an upper portion or chamber 54 of which is generally hemispherical having an opening 56 and a lower portion or chamber 58 of which is generally cylindrical and smaller in diameter than the hemispherical portion 54. Mounted over the opening 56 is a diaphragm 60 made, for example, of Viton (trademark). A tuning fork 64 is mounted in the lower portion 58 of the housing 50 out of the way of the hemispherical portion 54. An oscillator circuit 68 is coupled to the tuning fork to cause the tuning fork to vibrate, and a display 72 is provided to give a visual indication of the frequency and pressure being measured.

The diaphragm 60 is sealingly mounted over the opening 56 of the housing 50 to prevent introduction of ambient fluid into the housing. The housing 50 includes a working gas as discussed for the apparatus of FIG. 2. As the exterior pressure changes, the diaphragm 60 is caused to move inwardly in the housing (with pressure increase) or outwardly from the housing (with a pressur decrease) to thus cause a change in density of the gas contained in the housing. The frequency of vibration of the tuning fork 64, of course, tracks the change in the gas density to provide the desired measurement.

The portion 54 of the housing 50 is formed with hemispherical walls so that they will act to prevent movement of the diaphragm into contact with the tuning fork 64 and will allow compression of most of the gas in the housing 50 into chamber 58. Obviously, contact of the tuning fork 64 by the diaphragm 60 would interfere with the operation of the apparatus and the measurement being taken. A screen 76 could also be provided at the junction of the hemispherical portion 54 and the lower portion 58 to further block any movement of the diaphragm towards the tuning fork 64.

The FIG. 3 embodiment can achieve greater pressure measurement ranges than the FIG. 2 embodiment because higher compression ratios can be obtained with the FIG. 3 embodiment than with the FIG. 2 embodiment. Stated another way, there is too much dead space which cannot be compressed with a bellows arrangement, unlike a diaphragm arrangement wherein most of the interior space can be compressed. That is, as the exterior pressure increases, the diaphragm is able to move into the chamber 54 to contact and conform to the hemispherical walls of the chamber and thereby take up most of the space within the housing 50.

FIG. 4 shows a gas density/temperature transducer of a structure known as a "filled thermal system". This structure is comprised of a first generally rigid hollow housing 80, a second generally rigid hollow housing 84, and a capillary tube 88, having an internal volume substantially less than the volume of housing 80, interconnecting the two housings. A tuning fork 86 is mounted in the housing 84, and is coupled to an oscillator circuit 88 which, in turn, is coupled to a display 90. Advantageously, the housings 80 and 84 and the capillary 88 is made of a material possessing high strength at high temperatures, such as stainless steel or Inconel (trademark). Also, noble gases are a preferred fluid for placement in the housings 80 and 84 and the capillary tube 88.

To measure temperature changes, the housing 88 is exposed to the medium whose temperature is to be measured so that the fluid contained in the housing will increase in temperature and expand, or decrease in temperature and contract, depending upon the temperature of the medium. With such expansion or contraction, the fluid molecules are either driven from housing 80 toward housing 84 or vice versa. Thus, the gas density in housing 84 is caused to change with a change in temperature of the gas in housing 80. Because of the remoteness of housing 84 from housing 80 and the insulative nature and size of the capillary tube 88, the temperature of the gas in housing 84 does not appreciably change with the change in temperature of the gas in housing 80. With a change in gas density in housing 84, the frequency of vibration of the tuning fork 86 changes to provide a measure of the temperature change.

In the event that temperature contamination of the fluid in housing 84 occurs to the extent of introducing significant error, a temperature sensor could be placed in the housing 84 to track temperature changes there and then the temperature determination made by the oscillator 88 could be corrected to account for the unwanted temperature changes in the housing 84. This could be done by using conventional microprocessor or circuit correction techniques. And, of course, such temperature compensation might be desirable for all the fluid density transducer embodiments described herein.

The selection of argon or other noble gases below argon on the periodic chart for use as the working fluid in housing 80 is made because such gases have critical temperatures below $-100°$ C. and so will not condense at any pressure above that temperature. Thus such gases behave as nearly ideal gases for all pressures and temperatures normally encountered where temperature or pressure measurements are desired.

The FIG. 5 apparatus is a gas density/acceleration transducer constructed similar to the transducer of FIG. 2, but further including a piece of material 100 of known mass mounted on the flat wall 104 of a bellows 108. As the FIG. 5 apparatus is accelerated (or decelerated) in the direction indicated by the arrow, the mass 100 tends to compress (or expand) the bellows 108 and thus the gas contained in housing 112. The resulting change in density is detected by a tuning fork 116 and oscillator 120. The change in frequency of vibration of the tuning fork 116 is proportional to the change in acceleration of the apparatus and so can provide a measure of such acceleration.

Figure 6:
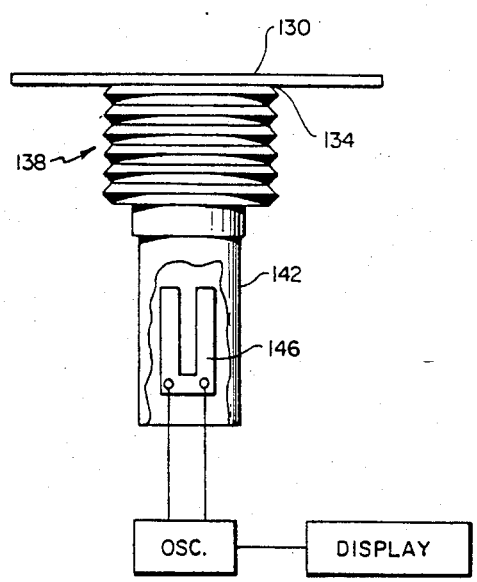
FIG. 6 is a side, elevational, partially cut-away view of a gas density/force transducer.

The FIG. 6 apparatus is for a gas density/force transducer, again constructed similar to the apparatus of FIG. 2. However, a generally flat receiving plate 130 is mounted on the flat wall 134 of a bellows 138. The apparatus of FIG. 6 is positioned so that the receiving plate 130 is generally horizontal (but it could be used in other orientations). Forces, such as the weight of an object, are applied to the receiving plate 130 which causes the bellows 138 to compress (or expand) and this, in turn, increases (or decreases) the density of gas in housing 142 surrounding a tuning fork 146. The frequency of vibration of the tuning fork 146 is thus caused to change and this change is proportional to the force applied to the bellows 138 which is to be measured.

Figure 7:
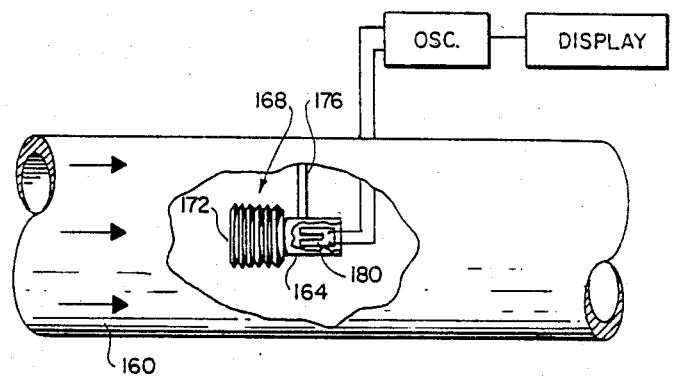
FIG. 7 is a side, elevational, partially cut-away view of a gas density/flow velocity transducer.

FIG. 7 shows apparatus for measuring the velocity of a medium flowing in a conduit 160. The apparatus is essentially the same as that of FIG. 2 and includes a housing 164, and a bellows 168 having a generally flat end wall 172. The apparatus is positioned in the conduit 160 by a brace 176 so that the end wall 172 of the bellows 168 faces "upstream". Higher velocities of the medium will cause a greater compression of the bellows 168 and thus a change in the density of the working gas in the housing 164. This will be detected by a change in the frequency of vibration of tuning fork 180 to provide a readout of the flow velocity of the medium. Correction for pressure changes in the conduit 160 must be made, as the apparatus will also be influenced by said pressure changes.

Figure 8:
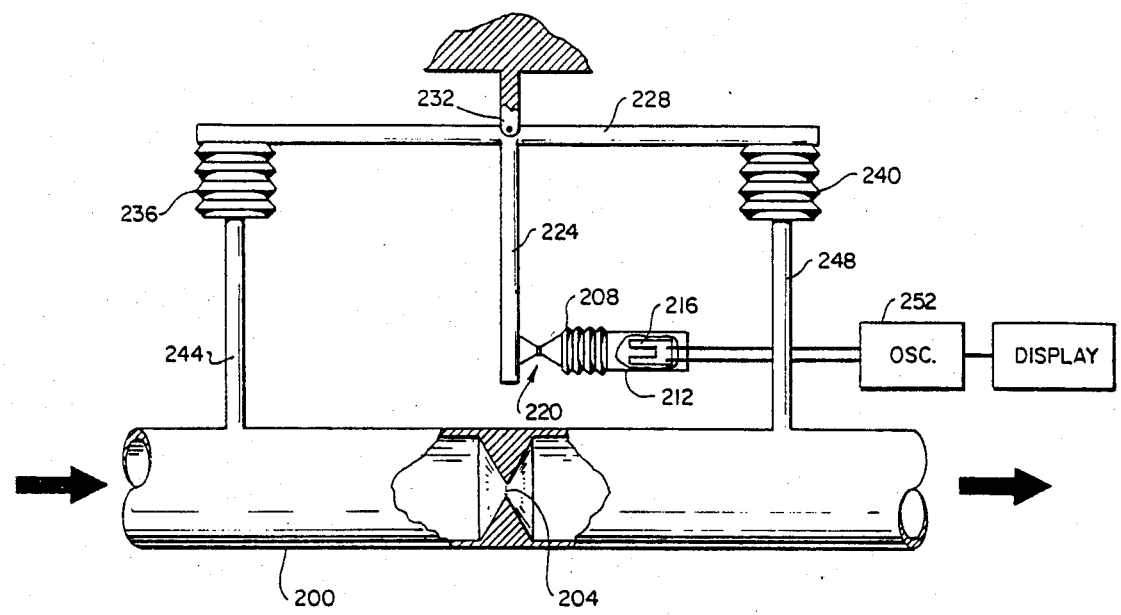
FIG. 8 is a side, elevational, partially cut-away view of a gas density/differential pressure transducer.

The FIG. 8 apparatus is for measuring differential pressure, for example, in a medium flowing in a conduit 200 through an orifice 204. Of course, the apparatus of FIG. 8 could be used for measuring the pressure differential in a variety of situations. The apparatus includes a bellows 208, housing 212, and tuning fork 216 in the configuration described earlier. The bellows 208 is coupled by way of a pivot or hinge coupling 220 to a pivot rod 224. The pivot rod 224 extends laterally of a rocker beam 228 which is mounted to rock or pivot about a fixed pivot hinge 232. Bellows 236 and 240 are mounted at respective ends of the beam 228, and each is coupled by respective tubes 244 and 248 to communicate with different parts of the conduit 200. The pressures of the medium flowing in the different parts of the conduit are different, and it is this difference which is to be measured.

Because the medium is flowing in the conduit 200 in the direction indicated by the arrows, the pressure in tube 244 would be higher than that in tube 248, and this pressure would operate through the bellows 236 against the left end of the beam, forcing it upwardly. The bellows 236 and 240 are provided to allow movement of the beam 228 with respect to the tubes 244 and 248. As the left end of the beam 228 moves upwardly, the pivot rod 224 is caused to move away from the housing 212, expanding the bellows 208 and thus the gas contained therein. The resulting decrease in density of the gas is detected by the tuning fork 216 and an oscillator 252. The magnitude of the change in gas density is proportional to the pressure differential between tubes 244 and 248.

Of course, if the medium flowing in the conduit 200 flows in the opposite direction of that indicated in the drawing, then the pressure in tube 248 would be higher than the pressure in tube 244 and so the pivot rod 224 would be caused to move toward the housing 212 to thus increase the density of the gas in the housing. This increase would be detected to again provide measure of the differential pressure in the conduit 200.

A particular structure for utilizing the gas density transducer of the present invention is shown in FIG. 8, but it should be understood that a variety of other structures could also be employed.

In the manner described, a variety of fluid density transducers can be provided for measuring parameters such as pressure, temperature, acceleration, force or weight and differential pressure. All such transducers make use of the phenomenon that a change in fluid density surrounding a vibratory element causes a change in frequency of vibration of the element. By appropriate selection of the dimensions of the vibratory element and of the working fluids, either high resolution or full range measurement can be obtained and, in some instances both can be achieved. The apparatus is relatively low in cost and yet is extremely rugged and reliable.

It is to be understood that the above-described arrangements are only illustrative of the principles of the present invention. Numerous modifications and alternative arrangements may be devised by those skilled in the art without departing from the spirit and scope of the present invention and the appended claims are intended to cover such modifications and arrangements. For example, although single-ended tuning forks were shown for each of the embodiments, single elongate bars, double-ended tuning forks, or other vibratable elements could also be used.

What is claimed is:

1. Gas density/force transducer apparatus comprising
    a hollow housing having first and second chambers which are in communication with one another, the housing surrounding the first chamber being collapsible and expandable and the housing surrounding the second chamber being generally rigid, said first chamber being equal to or larger in volume than said second chamber when expanded,
    a movable wall disposed on the housing on one side of said first chamber to vary the volume in the housing as the wall is moved,
    a gas contained in the housing,
    means for applying a force to the movable wall,
    a vibratory element disposed in the housing,
    means for causing the element to resonate at a frequency f, said frequency varying with variation in the density of the gas in the housing and thus in the force applied to the movable wall, and
    means for determining the frequency f.

2. The apparatus of claim 1, further comprising:
    a material of known mass attached to the movable wall to compress or expand the wall and the volume in the housing as the apparatus is accelerated or decellerated in a certain direction.

3. The apparatus of claim 1, further comprising:
    means for positioning the housing and movable wall in the stream of flow of a fluid whose velocity is to be measured so that the flow direction of the fluid is generally normal against the movable wall.

4. The apparatus of claim 1, further comprising:
    a movable member coupled to the movable wall and responsive to the pressure differential between two pressure sources for moving in a first direction if the pressure from one source is greater than the pressure from the other to thereby compress the movable wall and volume in the housing, and in a second direction if the pressure from the other source is greater than the pressure from the one source to thereby expand the wall and volume in the housing, the extent of movement of the member being proportional to the pressure differential between the sources.

5. Apparatus as in claim 4 wherein said movable member comprises
    a rocker arm mounted to pivot about an axis at or near the midpoint of the arm,
    bellows mounted at each end of the rocker arm to enable communication between the ends of the arm and a respective pressure source so that each pressure source operates through a respective bellows to apply a force to a respective end of the arm,
    a pivot arm attached to the rocker arm at about the midpoint thereof to extend laterally therefrom in the plane in which the rocker arm moves, and
    pivot coupling means joining the pivot arm to the movable wall.

6. A method of measuring force related parameters comprising
    (a) providing a hollow housing having first and second chambers which are in communication with one another, the first of which is collapsible and expandable and the second of which is generally rigid, said first chamber being equal to or larger in volume than said second chamber when expanded,
    (b) providing a movable wall at one side of the first chamber to vary the volume in the first chamber of the housing as a force is applied to the wall and the wall is moved,
    (c) providing an elongate bar mounted in the second chamber of the housing, said bar having a generally rectangular cross-section,
    (d) providing a gas in the housing to surround the bar,
    (e) causing the bar to resonate at a frequency f, said frequency varying with variation in the density of the fluid surrounding the bar,
    (f) placing the housing in a position so that the force to be measured acts on the wall to cause it to move, and
    (g) determining the frequency of vibration of the bar.

7. A method as in claim 6 wherein step (d) comprises providing a gas selected from the group consisting of argon, xenon, radon, krypton and freon.

8. A method as in claim 6 wherein step (d) comprises providing a gas selected from the group consisting of helium, neon, hydrogen, methane and carbon monoxide.

9. A method as in claim 6 wherein the force related parameter to be measured is acceleration, said method further including the step of providing a material of known mass attached to the movable wall, and wherein step (f) comprises positioning the housing in a body to be accelerated so that as the body is accelerated, the material causes the wall to compress or expand the volume in the housing.

10. A method as in claim 6 wherein the force related parameter to be measured is the weight of an object, and wherein step (f) comprises placing the object on the movable wall to cause the wall to either compress or expand the volume in the housing.

11. A method as in claim 6 wherein the force related parameter to be measured is flow velocity of a medium, and wherein step (f) comprises placing the housing in the stream of flow of the medium so that the movable wall faces generally in a direction opposite the direction of flow of the medium.

12. A method as in claim 6 wherein the force related parameter to be measured is differential pressure between two pressure sources, said method further including the step of providing a movable member which moves in a first direction if the pressure from one source is greater than the pressure from the other, and in a second direction if the pressure from the other source is greater than the pressure from the one source, with the amount of movement of the member being proportional to the pressure differential between the sources, and wherein step (f) comprises coupling the movable member to the movable wall so that as the movable member moves in the first direction, the movable wall and volume in the housing are compressed, and as the movable member moves in the second direction, the movable wall and volume in the housing are expanded.

* * * * *